United States Patent [19]
Nobori et al.

[11] Patent Number: 6,090,980
[45] Date of Patent: Jul. 18, 2000

[54] PREPARATION PROCESS OF IMINOTRIS (DIMETHYLAMINO) PHOSPHORANE

[75] Inventors: Tadahito Nobori; Takaomi Hayashi; Katsuhiko Funaki; Atsushi Shibahara; Isao Hara; Shinji Kiyono; Kazumi Mizutani; Usaji Takaki, all of Kanagawa, Japan

[73] Assignee: Mitsui Chemicals, Inc., Japan

[21] Appl. No.: 09/201,655

[22] Filed: Dec. 1, 1998

[30] Foreign Application Priority Data

Dec. 4, 1997 [JP] Japan .................................. 9-334495

[51] Int. Cl.[7] ...................................................... C07F 9/06
[52] U.S. Cl. ........................................................... 564/12
[58] Field of Search ................................................. 564/12

[56] References Cited

PUBLICATIONS

Koidan et al, "Some Properties of Phosphorimidic Triamides", Journal of General Chemistry USSR, vol. 52, No. 9, Feb. 20, 1983, pp. 1779–1787.

Chemical Abstracts, vol. 093, No. 8, Aug. 25, 1980, Columbus, Ohio, Abstract No. 087657, Marchenko et al, "Ammonolysis of Triamidohalophosphonium Halides".

Marchenko et al, "N"–unsubstituted Phosphorimidic Triamides", Journal of General Chemistry USSR, vol. 48, No. 12/2, Jun. 10, 1979, p. 2529.

Issleib et al, "Dimethylaminoiminophosphorane", Syn. Inorg. Metal–Org. Chem. (Simoai), 1973, vol. 3 (3), pp. 255–266.

Database WPI, Section Ch, Week 9903, Derwent Publications Ltd., London, GB, Class E11, AN 99–029065, Japanese Patent Publication No. 97–0338821, 1998.

*Primary Examiner*—Shailendra Kumar
*Attorney, Agent, or Firm*—Burns, Doane, Swecker, & Mathis, L.L.P.

[57] ABSTRACT

A process is provided for preparing iminotris (dimethylamino)phosphorane at high purity and high yield from aminotris(dimethylamino)phosphonium chloride. Aminotris(dimethylamino)phosphonium chloride is first reacted with an aqueous solution of the hydroxide of an alkali metal or alkaline earth metal in the presence of a solvent in which the chloride and hydroxide of the alkali metal or alkaline earth metal are sparingly soluble, whereby iminotris(dimethylamino)phosphorane is formed. After water is dissolved off at a temperature of 70° C. or lower from the reaction mixture, solids are removed from the thus-concentrated reaction mixture by solid-liquid separation. The resultant mother liquor is then distilled to obtain iminotris(dimethylamino)phosphorane.

19 Claims, No Drawings

PREPARATION PROCESS OF IMINOTRIS (DIMETHYLAMINO) PHOSPHORANE

BACKGROUND OF THE INVENTION a) Field of the Invention

This invention relates to a simple and effective process for preparing iminotris(dimethylamino)phosphorane [also called "2,2,2-tris(dimethylamino)-2$\gamma^5$-phosphazene], namely, [(CH$_3$)$_2$N]$_3$P=NH from aminotris(dimethylamino) phosphonium chloride, namely, [(CH$_3$)$_2$N]$_3$P$^+$(NH$_2$),Cl$^-$. Iminotris(dimethylamino)phosphorane is an important compound as a synthesis intermediate for a phosphazene base, a phosphazenium compound or the like, which is extremely useful as a polymerization catalyst for alkylene oxides.

b) Description of the Related Art

Processes for the preparation of iminotris(dimethylamino) phosphorane, which comprise reacting aminotris (dimethylamino)phosphonium chloride and the methoxide of an alkali metal in methanol or aminotris(dimethylamino) phosphonium tetrafluoroborate and the methoxide of an alkali metal in methanol, in which these reactants are soluble, are disclosed in Nachr. Chem. Tec. Lab., 38(10), 1216, 1990 or Liebigs Ann., 1067, 1996, respectively. The use of such a reactant-soluble solvent therefore results in a reaction mixture with unreacted portions of the reactants dissolved therein. The reaction mixture also contains the chloride or tetrafluoroborate of alkali metal by-produced in the reaction, and this by-product is relatively soluble in such a solvent. Therefore, these unreacted reactants and by-product cannot be fully removed by filtration. It is hence necessary to subject the filtrate to distillation for purification. Nonetheless, the yield of iminotris(dimethylamino) phosphorane after the distillation of the above-described filtrate is not satisfactory. To the best of the inventors' knowledge, there is no report on use of an aqueous solution of the hydroxide of an alkali metal or alkaline earth metal, which is more widely used in industry, upon preparation of iminotris(dimethylamino)phosphorane from aminotris (dimethylamino)phosphonium chloride.

J. Organometallic Chem., 71, 164, 1974 discloses a process for obtaining iminotris(dimethylamino)phosphorane by hydrolyzing trimethylsilyliminotris(dimethylamino) phosphorane in the presence of an acid catalyst. The reactant, trimethylsilyliminotris(dimethylamino) phosphorane, is however prepared from trimethylsilyl azide, which has extremely high explosibility as described on page 162 of this publication. This still remains as unsolved problem from the industrial viewpoint.

SUMMARY OF THE INVENTION

An object of the present invention is therefore to provide a safe process and an effective process for obtaining iminotris(dimethylamino)phosphorane from aminotris (dimethylamino)phosphonium chloride, in that as a base to be reacted with the chloride, the hydroxide of an alkali metal or alkaline earth metal, said hydroxide being industrially more advantageous, can be used as an aqueous solution and further in that the process assures that iminotris (dimethylamino)phosphorane can be obtained with high reaction results and with high purity and yield after distillation.

To achieve the above-described object, the present inventors have proceeded with an extensive investigation. As a result, it has been found that a reaction of aminotris (dimethylamino)phosphonium chloride with an aqueous solution of the hydroxide of an alkali metal or alkaline earth metal in a particular solvent makes it possible to substantially use up aminotris(dimethylamino)phosphonium chloride and to form iminotris(dimethylamino)phosphorane in an extremely high reaction yield. It has also been found that removal of at least water from the reaction mixture by distillation at a specific temperature or lower results in practically no decomposition of the target product and in full precipitation of remaining unreacted alkali metal or alkaline earth metal hydroxide and the corresponding metal chloride, which has been by-produced in the reaction, thereby permitting easy separation of these solid components by solid-liquid separation. In addition, it has also been found that distillation of the mother liquor thus obtained by the elimination of water and such solid components as described above makes it possible to obtain iminotris(dimethylamino) phosphorane with surprisingly high distillation yield and high purity. Consequently it has been found that iminotris (dimethylamino)phosphorane is obtained with sufficiently high overall yield based on the aminotris (dimethylamino) phosphonium chloride. These findings have led to the completion of the present invention.

Specifically, the present invention provides a process for the preparation of iminotris(dimethylamino)phosphorane, which comprises:

reacting aminotris(dimethylamino)phosphonium chloride with an aqueous solution of the hydroxide of an alkali metal or alkaline earth metal in the presence of a solvent in which the chloride and hydroxide of said alkali metal or alkaline earth metal are sparingly soluble, whereby iminotris(dimethylamino) phosphorane is formed;

distilling off water at a temperature of 70° C. or lower from the reaction mixture;

removing solids from the thus-distilled reaction mixture by solid-liquid separation; and then distilling the resultant mother liquor to obtain iminotris (dimethylamino)phosphorane.

According to the process of the present invention, iminotris(dimethylamino)phosphorane can be safely obtained from aminotris(dimethylamino)phosphonium chloride. Moreover, the process of the present invention makes it possible to prepare iminotris(dimethylamino)phosphorane with high purity and high yield by using an alkali metal or alkaline earth metal hydroxide which is more advantageous from the industrial viewpoint.

DETAILED DESCRIPTION OF THE INVENTION AND PREFERRED EMBODIMENTS

Illustrative of the solvent required in the practice of the process of the present invention, in which the chloride and hydroxide of the alkali metal or alkaline earth metal are sparingly soluble, are aliphatic hydrocarbons such as n-pentane, n-hexane and cyclohexane, ethers such as dimethyl ether, diethyl ether, diisopropyl ether, dibutyl ether, tetrahydrofuran, 1,4-dioxane, ethylene glycol dimethyl ether, diethylene glycol dimethyl ether, anisole, o-dimethoxybenzene, ethyl phenyl ether, butyl phenyl ether and o-diethoxybenzene; aromatic hydrocarbons such as benzene, toluene, xylene, ethylbenzene, cumene, mesitylene, tetralin, butylbenzene, p-cymene, diethylbenzene, diisopropylbenzene, triethylbenzene, cyclohexylbenzene, dipentylbenzene and dodecylbenzene; and halogenated aromatic hydrocarbons such as chlorobenzene, o-dichlorobenzene, m-dichlorobenzene, 1,2, 4-trichlorobenzene, bromobenzene, o-dibromobenzene, bromochlorobenzene, o-chlorotoluene, p-chlorotoluene, p-chloroethylbenzene and 1-chloronaphthalene.

No particular limitation is imposed on the required solvent for use in the present invention, insofar as the solvent in which the chloride and hydroxide of the alkali metal or alkaline earth metal are sparingly soluble in the solvent, and insofar as the preparation process of the present invention is not impaired.

Among these, preferred examples include ethers having 4-8 carbon atoms, such as diethyl ether, diisopropyl ether, dibutyl ether, tetrahydrofuran, 1,4-dioxane, ethylene glycol dimethyl ether, diethylene glycol dimethyl ether, anisole, o-dimethoxybenzene and ethyl phenyl ether; aromatic hydrocarbons having 6 to 10 carbon atoms, such as benzene, toluene, xylene, ethylbenzene, cumene, mesitylene, tetralin, butylbenzene, p-cymene and diethylbenzene; and chlorinated aromatic hydrocarbons having 6 to 8 carbon atoms, such as chlorobenzene, o-dichlorobenzene, m-dichlorobenzene, o-chlorotoluene, p-chlorotoluene and p-chloroethylbenzene.

Of these preferred examples, those having boiling points higher than water are more preferred.

These solvents may be used either singly or in combination.

No particular limitation is imposed on the amount of the solvent to be used. In general, however, the solvent may be used in an amount of 200 parts by weight or less, preferably 1.0 to 100 parts by weight, more preferably 1.5 to 20 parts by weight per part by weight of aminotris(dimethylamino) phosphonium chloride as the starting material. The chloride may be completely dissolved in the solvent, or may remain partially or wholly insoluble there.

No particular limitation is imposed on the process for the preparation of aminotris(dimethylamino)phosphonium chloride for use in the process of the present invention insofar as the process of the present invention is impaired.

Usable examples include aminotris(dimethylamino) phosphonium chloride contained along with by-produced ammonium chloride in a reaction mixture obtained by reacting phosgene with hexamethylphosphoric triamide and further with ammonia as disclosed in Liebigs Ann. 1066, 1996, or isolated from the reaction mixture; and aminotris (dimethylamino)phosphonium chloride contained along with by-produced dimethylammonium chloride and/or ammonium chloride in a reaction mixture obtained by reacting 1 molecule of phosphorus pentachloride with 3 molecules of dimethylamine and further reacting with 1 molecule of ammonia as disclosed in Liebigs Ann. 1067, 1996, or isolated from the reaction mixture.

A further example of aminotris(dimethylamino) phosphonium chloride can be one contained in or has been isolated from a reaction mixture obtained by a synthesis process involving reaction of phosphorus pentachloride with dimethylamine and further with ammonia. The synthesis process comprises:

reacting phosphorus pentachloride and dimethylamine at a molar ratio of 1 to 5.80–6.30 and a temperature of from 0 to 80° C. under an absolute pressure of from 0.001 to 1.00 MPa in the presence of an aromatic hydrocarbon while controlling water, which is to be introduced into a reaction system, at 0.9 wt. % or lower based on the phosphorus pentachloride, whereby tris (dimethylamino)phosphonium dichloride is formed; and then reacting the tris(dimethylamino)phosphonium dichloride with ammonia in an amount of from 1.8 to 50 mol per mol of the thus-used phosphorus pentachloride at a temperature of from 0 to 60° C. under an absolute pressure of from 0.001 to 1.00 MPa.

Aminotris(dimethylamino)phosphonium chloride can be by-produced upon preparation of tetrakis[tris (dimethylamino)phosphoranylidenamino]phosphonium chloride by reacting phosphorus pentachloride and iminotris (dimethylamino)phosphorane. In addition, aminotris (dimethylamino)phosphonium chloride is formed as a result of a reaction between iminotris(dimethylamino) phosphorane and hydrogen chloride. It is also possible to use thus formed aminotris(dimethylamino)phosphonium chloride in the process of the present invention.

When aminotris(dimethylamino)phosphonium chloride contained in a reaction mixture as described above is used, the reaction mixture may be used as is if its solvent is the same as the solvent in the present invention. Otherwise, the aminotris(dimethylamino)phosphonium chloride can be used after distilling off the solvent by a suitable method and instead, adding the solvent required in the practice of the present invention.

Examples of the alkali metal or alkaline earth metal hydroxide in the process of the present invention include the hydroxides of alkali metals such as lithium, sodium, potassium, rubidium and cesium; and the hydroxides of alkaline earth metals such as magnesium, calcium, strontium and barium. Among these, the hydroxides of alkali metals are preferred, with sodium hydroxide and potassium hydroxide being more preferred.

These alkali metal hydroxides and alkaline earth metal hydroxides can be used either singly or in combination.

The alkali metal or alkaline earth metal hydroxide is used as an aqueous solution. The concentration of the aqueous solution varies depending on the kind of the alkali metal or alkaline earth metal but may be 80 wt. % or lower in general, with 5 to 60 wt. % being preferred.

No particular limitation is imposed on the amount of the alkali metal or alkaline earth metal hydroxide. However it may be used in an amount ranging generally from 0.7 to 3.0 gram equivalents, preferably from 0.9 to 2.0 gram equivalents, more preferably from 1.0 to 1.5 gram equivalents per mol of aminotris (dimethylamino) phosphonium chloride.

If dimethylammonium chloride and/or ammonium chloride, which consume the alkali metal or alkaline earth metal hydroxide, is concurrently present in the system, it is necessary to additionally incorporate the hydroxide in an amount equivalent to the total gram equivalents of these compounds.

According to the process of the present invention, aminotris(dimethylamino)phosphonium chloride and the aqueous solution of the alkali metal or alkaline earth metal hydroxide are reacted in the presence of the solvent in which the chloride and hydroxide of the alkali metal or alkaline earth metal are sparingly soluble. There is no particular limitation as to how they should be brought into contact with each other. In general, however, aminotris(dimethylamino) phosphonium chloride may be added first to the solvent, followed by the addition of the aqueous solution of the alkali metal or alkaline earth metal hydroxide.

The reaction temperature may be generally 70° C. or lower, preferably 10 to 65° C., more preferably 15 to 60° C. The reaction time may be generally 24 hours or less, preferably 0.01 to 10 hours, more preferably 0.02 to 5 hours. The reaction is usually conducted under atmospheric pressure, although it can be performed under reduced pressure, atmospheric pressure or elevated pressure.

This reaction is accompanied by dehydrochlorination. Concurrently with the formation of iminotris (dimethylamino)phosphorane, hydrogen chloride is by-produced. The hydrogen chloride reacts with the alkali metal or alkaline earth metal hydroxide, and forms the alkali metal or alkaline earth metal chloride and water. Most of the alkali metal or alkaline earth metal chloride thus formed usually precipitates as a solid.

In an ordinary case, the reaction mixture consists of three phases which are a water phase, an organic phase and a solid phase, although this varies depending on the solvent used, the concentration of the aqueous solution of the alkali metal or alkaline earth metal hydroxide and other conditions. The resultant iminotris(dimethylamino)phosphorane is liquid and is generally dissolved in both the water phase and the organic phase.

As has been described above, iminotris(dimethylamino) phosphorane can be formed with extremely high yield by using an aqueous solution of an alkali metal or alkaline earth metal hydroxide which is more widely used in industry.

In the process of the present invention, at least water is distilled off from the reaction mixture while controlling the temperature of the reaction mixture at 70° C. or below. The solids in the reaction mixture may be removed beforehand if necessary. Any method may be used for distilling off water insofar as the object of the process of the present invention is not impaired. For example, water can be driven off by distillation under reduced pressure or by flowing an inert gas and allowing it to flow out together with the water. Vacuum distillation is employed usually. As a method for conducting this vacuum distillation, either simple distillation or rectification can be chosen depending on the case. Further, it can be conducted either batchwise or continuously.

Conditions of the thus concentrated reaction mixture after the removal of water by distillation vary depending on the boiling point and amount of the solvent used. If the solvent is one having a boiling point lower than water, the solvent is allowed to evaporate off either before or together with water so that the solvent does not remain either absolutely or substantially in the thus concentrated reaction mixture. If the solvent is one having a boiling point higher than water, on the other hand, the solvent substantially remains in the concentrated solution although a small portion of the solvent may evaporate off together with water. It is preferred to use a solvent having a boiling point higher than water so that the solvent is allowed to remain by distilling off water in advance or by distilling off water together with a portion of the solvent. Iminotris(dimethylamino)phosphorane has a boiling point much higher than water so that subsequent to removal of water by distillation, it remains in the resultant concentrated reaction mixture.

In the process of the present invention, it is essential that at least water be distilled off from the reaction mixture while controlling the temperature of the reaction mixture at 70° C. or lower. A temperature higher than this temperature leads to an extreme reduction in the yield of iminotris (dimethylamino)phosphorane, because at such a high temperature, iminotris(dimethylamino)phosphorane reacts with water and formation of aminohydroxytris (dimethylamino)phosphorane or the like becomes significant. The distillation temperature may range preferably from 10 to 65° C., more preferably from 15 to 60° C. The pressure upon conducting the vacuum distillation varies depending on the distillation temperature.

Water is distilled off as described above. The lower the water content in the concentrated mixture after the removal of water by distillation, the better. The water content is generally 3 mol % or lower based on the iminotris (dimethylamino)phosphorane contained in the concentrated mixture. This value can be easily achieved by conventional vacuum distillation at 70° C. or lower.

In the concentrated mixture obtained as described above, iminotris(dimethylamino)phosphorane is contained as an oil or is dissolved in the remaining solvent.

When the alkali metal or alkaline earth metal hydroxide is used in excess in the reaction, the remaining unreacted hydroxide is already in a solid form in the concentrated reaction mixture after removal of the water. The alkali metal or alkaline earth metal chloride by-produced in the reaction remains entirely as a solid in the concentrated reaction mixture, when the solid-liquid separation is not conducted before the removal of the water.

Even when the solid-liquid separation is conducted before the removal of the water, a portion of the chloride, which is dissolved in water, remains in the liquid. This portion of the chloride comes out in the concentrated reaction mixture as precipitate as a result of the removal of the water.

These solid components are then removed from the concentrated mixture by solid-liquid separation. When the solvent remains, if needed, the solid-liquid separation may be conducted after either partial or full removal of the solvent.

No particular limitation is imposed on the manner of the solid-liquid separation, but a conventional method such as filtration or centrifugation may be used in general. Even when heated to a temperature higher than 70° C., the mother liquor which has been obtained by distilling off water and removing solid components as described above is no longer accompanied with the problem that an extreme reduction may take place in the yield of the target product.

In the process of the present invention, water is distilled off at 70° C. or lower, solids are removed by solid-liquid separation, and the resultant mother liquor is then distilled to separate the solvent, if remains, and to obtain iminotris (dimethylamino)phosphorane. This distillation is usually rectified under reduced pressure by using a rectifying tower, for example, a packed tower, which makes use of a conventional packing material such as Raschig rings or Berl saddles, or a tray tower such as a bubble cap tower or a perforated tray tower. The rectification can be conducted either batchwise or continuously. Upon distilling out iminotris(dimethylamino)phosphorane, the top temperature is generally 170° C. or lower, preferably from 55 to 155° C., more preferably from 75 to 135° C. Upon conducting the distillation, the pressure varies depending on the temperature.

By this distillation, high-purity iminotris(dimethylamino) phosphorane can be obtained with sufficiently high distillation yield.

As has been described above, the formation yield and distillation yield of iminotris(dimethylamino)phosphorane are both sufficiently high, thereby making it possible to obtain iminotris(dimethylamino)phosphorane with high overall yield from aminotris(dimethylamino)phosphonium chloride.

The present invention will next be described in further detail by examples. However, these examples should be interpreted merely as illustrative rather than as limiting.

EXAMPLE 1

In a 2-l reactor fitted with a stirrer, a thermometer and a dropping funnel, 1.09 kg of o-dichlorobenzene were weighed, followed by the addition of 250 g (1.16 mol) of aminotris(dimethylamino)phosphonium chloride. The contents were heated to 50° C., at which 114 g of a 45 wt. % aqueous solution of sodium hydroxide, said solution containing 1.28 mol (equivalent to 1.1 gram equivalents based on the chloride) of sodium hydroxide, were added dropwise over 20 minutes. After completion of the dropwise addition, the resulting mixture was stirred at the same temperature for 3 hours and was then allowed to cool down to room temperature in about 30 minutes.

The reaction mixture consisted of three phases, which are a water phase, an organic phase and a solid phase. The reaction mixture was vigorously agitated, and a portion of the reaction mixture was sampled and subjected to a quantitative analysis by gas chromatography. Iminotris(dimethylamino)phosphorane was found to have been formed with a reaction yield of 99 mol %. While maintaining the temperature of the reaction mixture at 55° C., the pressure was gradually lowered from 118 mmHg to 10 mmHg so that water and o-dichlorobenzene were distilled off by simple distillation. The amounts of the water and o-dichlorobenzene so distilled off were 83.4 g and 78.5 g, respectively. Water was therefore removed in its entirety as far as calculation is concerned.

Subsequently, 870 g of o-dichlorobenzene were distilled off at 55° C. and 10 mmHg. The resulting concentrated reaction mixture was filtered, whereby a clear, pale yellow filtrate was obtained. Solids which had been removed by the filtration were washed twice with 70.0 g of o-chlorobenzene. A solution, which had been obtained by combining the filtrate and the washings, was charged into a pear-shaped 750-ml flask fitted with a rectifying column constructed of a column of 30 mm in diameter and 400 mm in total length and Berl saddles made of stainless steel (McMahon packing) and packed in the column. Under a pressure of 10 mmHg, a forerunning was collected at top temperatures of from 52.5 to 54.0° C., so that the o-dichlorobenzene was distilled off substantially in its entirety.

Under the same pressure, 17.5 g of an initial distillation fraction were then collected around a top temperature of 96.5° C. and 158 g of a main distillation fraction were collected further in a top temperature range of from 96.5 to 98.0° C. By repeating an operation that the temperature of contents of the flask was slightly raised whenever distillation decreased, 14.2 g of a last distillation fraction were collected at top temperatures of from 96.0 to 98.0° C. A residue occurred only in an extremely small amount. Each of the fractions was in the form of a colorless clear liquid.

Their $^1$H-NMR and $^{31}$P-NMR spectra were consistent with those of standard iminotris(dimethylamino)phosphorane. By gas chromatography, their purities were analyzed to be 99.0, 99.9 and 99.9 wt. % and hence to be extremely high. The distillation yield of iminotris(dimethylamino)phosphorane as calculated by combining the initial distillation fraction, the main distillation fraction and the last distillation fraction [the distillation yield indicates the yield of iminotris(dimethylamino)phosphorane based the same compound formed by the reaction; this will hereinafter apply equally] was 92 mol %. The iminotris(dimethylamino)phosphorane was obtained with an overall yield as high as 91 mol % based on the aminotris(dimethylamino)phosphonium chloride as the reactant.

Comparative Example 1

The procedures of Example 1 were repeated in exactly the same manner except that upon distilling off water and o-dichlorobenzene from the reaction mixture, the simple vacuum distillation with the reaction mixture controlled at 55° C. was replaced by simple atmospheric distillation at 104 to 105° C. An initial distillation fraction, a main distillation fraction and a last distillation fraction were obtained in amounts of 4.89 g, 53.4 g and 5.92 g, respectively. The purities of the respective fractions were 98.9, 99.8 and 99.8 wt. %. The distillation yield as calculated by combining the initial distillation fraction, the main distillation fraction and the last distillation fraction was 32 mol %, and the overall yield was as low as 31 mol %.

A great deal of solids remained in a still. As a result of an analysis, the solids were found to comprise aminohydroxytris(dimethylamino)phosphorane as a principle component. This compound is believed to have occurred as a result of an addition reaction of water with the resulting iminotris(dimethylamino)phosphorane at elevated temperatures.

Comparative Example 2

The procedures of Example 1 were repeated in exactly the same manner except that in place of o-dichlorobenzene and the 45 wt. % aqueous solution of sodium hydroxide, methanol and sodium methoxide were used in the same weight and in the same gram equivalents, respectively. The reaction mixture consisted of two phases, that is, an organic phase and a solid phase. As a result of a similar quantitative analysis as in Example 1, iminotris(dimethylamino)phosphorane was found to be formed with a reaction yield of 97 mol %.

The reaction mixture was filtered, whereby a colorless clear filtrate was obtained. Solids which had been removed by the filtration were washed twice with 70.0 g of methanol. From a solution obtained by combining the filtrate and the washings, 1.02 kg of methanol were distilled off at 50° C. and 400 mmHg by simple distillation. The resulting concentrated mixture had a yellow color, and contained solids as a precipitate.

The concentrated mixture was charged in a flask fitted with a rectifying column similar to that employed in Example 1, and under a pressure of 400 mmHg and around a top temperature of 49° C., the methanol was distilled off as a fore-running substantially in its entirety. The residue was then rectified under a pressure of 10 mmHg in a similar manner as in Example 1. 12.0 g of an initial distillation fraction were collected around a top temperature of 96.5° C., 119 g of a main distillation fraction were collected in a top temperature range of from 96.5 to 98.0° C., and 11.0 g of a last distillation fraction were also collected. The amount of the distillation residue was 18.6 g. The purities of the respective distillation fractions were 99.1, 99.8 and 99.9 wt. %. The distillation yield of iminotris(dimethylamino)phosphorane as calculated by combining the initial distillation fraction, the main distillation fraction and the last distillation fraction dropped substantially to 70 mol %. The overall yield was 68 mol % based on the aminotris(dimethylamino)phosphonium chloride.

Comparative Example 3

The procedures of Example 1 were repeated in exactly the same manner except that the filtration was omitted, whereby an initial distillation fraction, a main distillation fraction and a last distillation fraction were obtained in amounts of 12.3 g, 111 g and 10.0 g, respectively. The residue was as much as 83.5 g and contained a great deal of solids. The purities of the respective distillation fractions were 99.0, 99.8 and 99.8 wt. %. The distillation yield as calculated by combining the initial distillation fraction, the main distillation fraction and the last distillation fraction was low, that is, 65 mol %, and the overall yield was 64 mol %.

EXAMPLE 2

The procedures of Example 1 were repeated in exactly the same manner except that in place of o-dichlorobenzene and the 45 wt. % aqueous solution of sodium hydroxide, toluene and a 50 wt. % aqueous solution of potassium hydroxide were used in the same weight and in the same gram equivalents, respectively. Iminotris(dimethylamino) phosphorane was formed with a reaction yield of 98 mol %. Further, water and toluene were distilled off by simple distillation by gradually changing the pressure from 118 mmHg to 100 mmHg while maintaining the temperature of the reaction mixture at 55° C. The amounts of the water and toluene removed by the distillation were 112 g and 766 g, respectively. Further, 140 g of toluene were distilled off at 55° C. and 100 mmHg. The concentrated mixture so obtained was filtered. Solids which had been removed by the filtration were washed twice with 70.0 g of toluene.

A solution, which had been obtained by combining the filtrate and the washings, was charged in a flask fitted with a rectifying column similar to that employed in Example 1, and under a pressure of 100 mmHg and around a top temperature of 52° C., the toluene was distilled off as a fore-running substantially in its entirety. Rectification was then conducted under a pressure of 10 mmHg in a similar manner as in Example 1. 15.5 g of an initial distillation fraction were collected around a top temperature of 96.5° C., 155 g of a main distillation fraction were collected in a top temperature range of from 96.5 to 98.0° C., and 15.4 g of a last distillation fraction were also collected in a top temperature range of from 96.0 to 98.0° C. The purities of the respective distillation fractions were 99.3, 99.8 and 99.9 wt. %. The distillation yield was 91 mol %. The overall yield was 89 mol %.

EXAMPLE 3

The procedures of Example 1 were repeated in exactly the same manner except that in place of o-dichlorobenzene, chlorobenzene was used in the same weight and as reaction conditions, 50° C. and 3 hours were changed to 55° C. and 0.5 hour. Iminotris(dimethylamino)phosphorane was formed with a reaction yield of 99 mol %. Further, water and chlorobenzene were distilled off by simple distillation by gradually changing the pressure from 118 mmHg to 50 mmHg while maintaining the temperature of the reaction mixture at 55° C. The amounts of the water and chlorobenzene removed by the distillation were 83.4 g and 789 g, respectively. Further, 210 g of chlorobenzene were distilled off at 55° C. and 50 mmHg. The concentrated mixture so obtained was filtered. Solids which had been removed by the filtration were washed twice with 70.0 g of chlorobenzene.

A solution, which had been obtained by combining the filtrate and the washings, was charged in a flask fitted with a rectifying column similar to that employed in Example 1, and under a pressure of 50 mmHg and around a top temperature of 53° C., the chlorobenzene was distilled off as a forerunning substantially in its entirety. Rectification was then conducted under a pressure of 10 mmHg in a similar manner as in Example 1. 23.0 g of an initial distillation fraction were collected around a top temperature of 96.5° C., 152 g of a main distillation fraction were collected in a top temperature range of from 96.5 to 98.0° C., and 6.09 g of a last distillation fraction were also collected in a top temperature range of from 96.0 to 98.0° C. The purities of the respective distillation fractions were 99.0, 99.9 and 99.8 wt. %. The distillation yield was 88 mol %. The overall yield was 87 mol %.

EXAMPLE 4

In a 5-l reactor fitted with a stirrer, a thermometer and a dropping funnel, 1.60 kg of tetrahydrofuran were weighed, followed by the addition of 250 g (1.16 mol) of aminotris (dimethylamino)phosphonium chloride. The contents were heated to 55° C., at which 2.29 kg of a 5.6 wt. % aqueous solution of barium hydroxide, said solution containing 0.83 mol (equivalent to 1.1 gram equivalents based on the chloride) of barium hydroxide, were added dropwise over 20 minutes. After completion of the dropwise addition, the resulting mixture was stirred at the same temperature for 30 minutes and was then allowed to cool down to room temperature in about 30 minutes. Iminotris(dimethylamino) phosphorane was formed with a reaction yield of 99 mol %.

While maintaining the temperature of the reaction mixture at 55° C., the pressure was gradually lowered from 650 mmHg to 100 mmHg so that water and tetrahydrofuran were distilled off by simple distillation. The amounts of the water and tetrahydrofuran so distilled off were 1.60 kg and 2.18 kg, respectively. The resulting concentrated mixture was filtered. Solids which had been removed by the filtration were washed twice with 110 g of tetrahydrofuran.

A solution, which had been obtained by combining the filtrate and the washings, was charged in a flask fitted with a rectifying column similar to that employed in Example 1, and under a pressure of 650 mmHg and around a top temperature of 52° C., the tetrahydrofuran was distilled off as a fore-running substantially in its entirety. Rectification was then conducted under a pressure of 10 mmHg in a similar manner as in Example 1. 12.9 g of an initial distillation fraction were collected around a top temperature of 96.5° C., 160 g of a main distillation fraction were collected in a top temperature range of from 96.5 to 98.0° C., and 14.4 g of a last distillation fraction were also collected in a top temperature range of from 96.0 to 98.0° C. Their purities were 99.2, 99.9 and 99.9 wt. %, respectively. The distillation yield was 91 mol %, and the overall yield was 90 mol %.

EXAMPLE 5

In a glass-lined, 5-l autoclave which had been purged with nitrogen gas, 417 g (2.00 mol) of phosphorus pentachloride were weighed. Into the autoclave, 2.50 kg of o-dichlorobenzene which had been rendered anhydrous beforehand by using molecular sieves 3A (its water content was 18 ppm by weight as measured by the Karl-Fischer moisture content measuring method) was charged under nitrogen gas pressure. The contents of water in dimethylamine and ammonia for use in this Example were lower than the detection limit, and the phosphorus pentachloride was anhydrous. Accordingly, the amount of water to be introduced into the autoclave can be approximated by the amount of water introduced as an impurity together with the solvent. At this stage, the amount of water in the reaction system was 0.011 wt. % based on the phosphorus pentachloride.

While stirring the contents of the autoclave, dimethylamine was introduced in a gaseous form at a rate of 84.0 g/hr for 6.5 hours. At this time, the reaction temperature was controlled to remain at 60° C. During the reaction, the pressure was 0.18 MPa (absolute pressure, this will hereinafter apply equally) at the maximum. From a reduction in the weight of a dimethylamine cylinder, the exact amount of the dimethylamine so introduced was determined to be 547 g (12.1 mol), that is, 6.05 mol per mol of the phosphorus pentachloride. Subsequent to completion of the introduction, stirring was continued at the same temperature for 1 hour. The reaction mixture was allowed to cool down to room temperature, and remaining gas was released from the autoclave. Ammonia was then introduced in a gaseous form at a rate of 77.0 g/hr for 4.0 hours into the autoclave. During the introduction of ammonia gas, the reaction temperature was controlled to remain at 40° C. Concerning the reaction pressure, an outlet valve was set at 0.25 MPa and the opening of the valve was controlled to hold this temperature. From a reduction in the weight of an ammonia cylinder, the exact amount of the ammonia so introduced was determined to be 309 g (18.1 mol), that is, 9.05 mol per mol of the phosphorus pentachloride.

Subsequent to completion of the introduction, stirring was continued at the same temperature for 2 hours. The reaction mixture was then allowed to cool down to room temperature, whereby a suspension in o-dichlorobenzene was obtained. As a result of an analysis, the suspension was found to contain 421 g (1.96 mol) of aminotris(dimethylamino) phosphonium chloride (yield: 98.0% based on the phosphorus pentachloride), 148 g (1.81 mol) of dimethylammonium chloride, and 331 g (6.19 mol) of ammonium chloride. Phosphorus pentachloride was not detected.

The suspension was charged in a 7-l reactor which was fitted with a stirrer, a thermometer and a dropping funnel. The suspension was heated to 50° C., at which 2.09 kg of a 20 wt. % aqueous solution of sodium hydroxide (10.5 mol as sodium hydroxide, including 8.0 mol to be consumed through reactions with the dimethylammonium chloride and ammonium chloride) were added dropwise over 20 minutes. After completion of the dropwise addition, the resulting mixture was stirred at the same temperature for 0.5 hour, and was then allowed to cool down to room temperature in about 30 minutes. The reaction mixture consisted of three phases, that is, a water phase, an organic phase and a solid phase.

According to an analysis of the liquid phase, iminotris (dimethylamino)phosphorane was found to be formed with a reaction yield of 98 mol % based on the aminotris (dimethylamino)phosphonium chloride in the employed suspension.

While maintaining the temperature of the reaction mixture at 55° C., the pressure was gradually lowered from 118 mmHg to 10 mmHg so that water and o-dichlorobenzene were distilled off by simple distillation. The amounts of the water and o-dichlorobenzene so distilled off were 1.85 kg and 1.23 kg, respectively. Water was therefore removed in its entirety as far as calculation is concerned. Subsequently, 570 g of o-dichlorobenzene were distilled off at 58° C. and 10 mmHg. The resulting concentrated mixture was filtered, whereby a clear, pale yellow filtrate was obtained. Solids which had been removed by the filtration were washed twice with 300 g of o-dichlorobenzene.

A solution, which had been obtained by combining the filtrate and the washings, was charged in a pear-shaped, 2-l flask fitted with a rectifying column similar to that employed in Example 1, and under a pressure of 10 mmHg and around a top temperature of 53° C., the o-dichlorobenzene was distilled off as a fore-running substantially in its entirety. Rectification was then conducted under the same pressure in a similar manner as in Example 1. 25.0 g of an initial distillation fraction were collected around a top temperature of 96.5° C., 274 g of a main distillation fraction were collected in a top temperature range of from 96.5 to 98.0° C., and 24.7 g of a last distillation fraction were also collected in a top temperature range of from 96.0 to 98.0° C. Their purities were 98.2, 99.8 and 99.9 wt. %, respectively. The distillation yield as calculated by combining the initial distillation fraction, the main distillation fraction and the last distillation fraction was 91 mol %, and the overall yield was 90 mol % based on the aminotris(dimethylamino) phosphonium chloride in the employed suspension.

What is claimed is:

1. A process for the preparation of iminotris (dimethylamino)phosphorane, which comprises:

reacting aminotris(dimethylamino)phosphonium chloride with an aqueous solution of the hydroxide of an alkali metal or alkaline earth metal in the presence of a solvent in which the chloride and hydroxide of said alkali metal or alkaline earth metal are sparingly soluble, whereby iminotris(dimethylamino) phosphorane is formed;

distilling off water at a temperature of 70° C. or lower from the reaction mixture;

removing solids from the thus-concentrated reaction mixture by solid-liquid separation; and then distilling the resultant mother liquor to obtain iminotris (dimethylamino)phosphorane.

2. A process according to claim 1, wherein said solvent in which said chloride and hydroxide of said alkali metal or alkaline earth metal are sparingly soluble is an ether having 4 to 8 carbon atoms, an aromatic hydrocarbon having 6 to 10 carbon atoms, or a chlorinated aromatic hydrocarbon having 6 to 8 carbon atoms.

3. A process according to claim 2, wherein said aminotris (dimethylamino)phosphonium chloride is contained in or has been isolated from a reaction mixture, which has been obtained by reacting 1 molecule of phosphorus pentachloride with 3 molecules of dimethylamine and further reacting with 1 molecule of ammonia.

4. A process according to claim 2, wherein said aminotris (dimethylamino)phosphonium chloride is contained in or has been isolated from a reaction mixture obtained by a synthesis process involving reaction of phosphorus pentachloride with dimethylamine and further with ammonia; and said synthesis process comprises:

reacting phosphorus pentachloride and dimethylamine at a molar ratio of 1 to 5.80–6.30 and a temperature of from 0 to 80° C. under an absolute pressure of from 0.001 to 1.00 MPa in the presence of an aromatic hydrocarbon while controlling water, which is to be introduced into a reaction system, at 0.9 wt. % or lower based on said phosphorus pentachloride, whereby tris (dimethylamino)phosphonium dichloride is formed; and then reacting said tris(dimethylamino)phosphonium dichloride with ammonia in an amount of from 1.8 to 50 mol per mol of the thus-used phosphorus pentachloride at a temperature of from 0 to 60° C. under an absolute pressure of from 0.001 to 1.00 MPa.

5. A process according to claim 4, wherein said hydroxide of said alkali metal or alkaline earth metal is sodium hydroxide or potassium hydroxide.

6. A process according to claim 5, wherein said aqueous solution of said hydroxide of said alkali metal or alkaline earth metal has a concentration in a range of from 5 to 60 wt. %.

7. A process according to claim 6, wherein upon distilling off water from said reaction mixture, said reaction mixture has a temperature in a range of from 10 to 65° C.

8. A process according to claim 1, wherein said aminotris (dimethylamino)phosphonium chloride is contained in or has been isolated from a reaction mixture, which has been obtained by reacting 1 molecule of phosphorus pentachloride with 3 molecules of dimethylamine and further reacting with 1 molecule of ammonia.

9. A process according to claim 8, wherein said aminotris(dimethylamino)phosphonium chloride is contained in or has been isolated from a reaction mixture obtained by a synthesis process involving reaction of phosphorus pentachloride with dimethylamine and further with ammonia; and said synthesis process comprises:

reacting phosphorus pentachloride and dimethylamine at a molar ratio of 1 to 5.80–6.30 and a temperature of from 0 to 80° C. under an absolute pressure of from 0.001 to 1.00 MPa in the presence of an aromatic hydrocarbon while controlling water, which is to be introduced into a reaction system, at 0.9 wt. % or lower based on said phosphorus pentachloride, whereby tris(dimethylamino)phosphonium dichloride is formed; and then reacting said tris(dimethylamino)phosphonium dichloride with ammonia in an amount of from 1.8 to 50 mol per mol of the thus-used phosphorus pentachloride at a temperature of from 0 to 60° C. under an absolute pressure of from 0.001 to 1.00 MPa.

10. A process according to claim 9, wherein said hydroxide of said alkali metal or alkaline earth metal is sodium hydroxide or potassium hydroxide.

11. A process according to claim 10, wherein said aqueous solution of said hydroxide of said alkali metal or alkaline earth metal has a concentration in a range of from 5 to 60 wt. %.

12. A process according to claim 11, wherein upon distilling off water from said reaction mixture, said reaction mixture has a temperature in a range of from 10 to 65° C.

13. A process according to claim 1, wherein said aminotris(dimethylamino)phosphonium chloride is contained in or has been isolated from a reaction mixture obtained by a synthesis process involving reaction of phosphorus pentachloride with dimethylamine and further with ammonia; and said synthesis process comprises:

reacting phosphorus pentachloride and dimethylamine at a molar ratio of 1 to 5.80–6.30 and a temperature of from 0 to 80° C. under an absolute pressure of from 0.001 to 1.00 MPa in the presence of an aromatic hydrocarbon while controlling water, which is to be introduced into a reaction system, at 0.9 wt. % or lower based on said phosphorus pentachloride, whereby tris(dimethylamino)phosphonium dichloride is formed; and then reacting said tris(dimethylamino)phosphonium dichloride with ammonia in an amount of from 1.8 to 50 mol per mol of the thus-used phosphorus pentachloride at a temperature of from 0 to 60° C. under an absolute pressure of from 0.001 to 1.00 MPa.

14. A process according to claim 13, wherein said hydroxide of said alkali metal or alkaline earth metal is sodium hydroxide or potassium hydroxide.

15. A process according to claim 13, wherein said aqueous solution of said hydroxide of said alkali metal or alkaline earth metal has a concentration in a range of from 5 to 60 wt. %.

16. A process according to claim 13, wherein upon distilling off water from said reaction mixture, said reaction mixture has a temperature in a range of from 10 to 65° C.

17. A process according to claim 1, wherein said hydroxide of said alkali metal or alkaline earth metal is sodium hydroxide or potassium hydroxide.

18. A process according to claim 1, wherein said aqueous solution of said hydroxide of said alkali metal or alkaline earth metal has a concentration in a range of from 5 to 60 wt. %.

19. A process according to claim 1, wherein upon distilling off water from said reaction mixture, said reaction mixture has a temperature in a range of from 10 to 65° C.

* * * * *